(12) United States Patent
Ding et al.

(10) Patent No.: US 11,845,981 B2
(45) Date of Patent: Dec. 19, 2023

(54) DELAYED PYROPHOSPHOROLYSIS ACTIVATED POLYMERIZATION

(71) Applicants: Shaofeng Ding, Santa Fe Springs, CA (US); Qiang Liu, Rancho Cucamonga, CA (US)

(72) Inventors: Shaofeng Ding, Santa Fe Springs, CA (US); Qiang Liu, Rancho Cucamonga, CA (US)

( * ) Notice: Subject to any disclaimer, the term of this patent is extended or adjusted under 35 U.S.C. 154(b) by 135 days.

(21) Appl. No.: 17/586,596

(22) Filed: Jan. 27, 2022

(65) Prior Publication Data
US 2023/0235386 A1  Jul. 27, 2023

(51) Int. Cl.
*C12Q 1/6853* (2018.01)
*C12Q 1/686* (2018.01)
*C12Q 1/6858* (2018.01)

(52) U.S. Cl.
CPC .......... *C12Q 1/6853* (2013.01); *C12Q 1/686* (2013.01); *C12Q 2525/186* (2013.01); *C12Q 2565/301* (2013.01)

(58) Field of Classification Search
CPC .... C12Q 1/6853; C12Q 1/686; C12Q 1/6844; C12Q 1/6848; C12Q 2537/143; C12Q 2565/301; C12Q 2525/186
See application file for complete search history.

(56) References Cited

PUBLICATIONS

Liu et al., "Multiplex dosage pyrophosphorolysis-activated polymerization: application to the detection of heterozygous deletions," 2006, BioTechniques, vol. 40, pp. 661-668. (Year: 2006).*

Lue and Peng, "Negative regulation of yeast telomerase activity through an interaction with an upstream region of the DNA primer," 1998, Nucleic Acids Research, vol. 26, pp. 1487-1494. (Year: 1998).*

Hummelshoj et al., "Locked nucleic acid inhibits amplification of contaminating DNA in real-time PCR," 2005, BioTechniques, vol. 38, pp. 605-610. (Year: 2005).*

Liu et al., "Multiplex dosage pyrophosphorolysis-activated polymerization: application to the detection of heterozygous deletions," 2006, BioTechniques, vol. 40, pp. 661-668. (Year: 2006). Cited in a previous Ofice Action.*

Lue and Peng, "Negative regulation of yeast telomerase activity through an interaction with an upstream region of the DNA primer," 1998, Nucleic Acids Research, vol. 26, pp. 1487-1494. (Year: 1998). Cited in a previous Ofice Action.*

* cited by examiner

*Primary Examiner* — Cynthia B Wilder
*Assistant Examiner* — Francesca Filippa Giammona

(57) ABSTRACT

A minimal-copy-ratio of templates is a problem in detecting early stage cancer where minimal copies of somatic cancer-specific mutations are targeted in the presence of large copies of wildtype genome DNA, commonly a 1/10,000 or even less minimal-copy-ratios between the mutant target and wildtype control templates. To overcome this problem, delayed pyrophosphorolysis activated polymerization (delayed-PAP) was developed which can delay product accumulation of the wildtype control to a much later time or cycle, such as by 15 cycles or by 30,000 folds. In the multiplex format, delayed-PAP is particularly useful to amplify not only the wildtype control but also mutant target templates accurately and consistently in the minimal-copy-ratio situation.

3 Claims, 2 Drawing Sheets
Specification includes a Sequence Listing.

```
                              SEQUENCE LISTING

<160> NUMBER OF SEQ ID NOS: 10

<210> SEQ ID NO 1
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is dideoxyC

<400> SEQUENCE: 1
gactctgagc cctctttcca aactactn                                         28

<210> SEQ ID NO 2
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is dideoxyC

<400> SEQUENCE: 2
gtctcaaaga ttccagaagt caggacan                                         28

<210> SEQ ID NO 3
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is dideoxyC

<400> SEQUENCE: 3
gactctgagc cctctttcca aacgactn                                         28

<210> SEQ ID NO 4
<211> LENGTH: 28
<212> TYPE: DNA
<213> ORGANISM: Homo sapiens
<220> FEATURE:
<221> NAME/KEY: misc_feature
<222> LOCATION: (28)..(28)
```

<223> OTHER INFORMATION: n is dideoxyC

<400> SEQUENCE: 4
gactctgagc cctctttcca aactaatn                28

<210> SEQ ID NO 5
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is dideoxyC

<400> SEQUENCE: 5
gtctcaaaga ttccagaagt cagtacan                28

<210> SEQ ID NO 6
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is dideoxyC

<400> SEQUENCE: 6
gtctcaaaga ttccagaagt caggaaan                28

<210> SEQ ID NO 7
<211> LENGTH: 22
<212> TYPE: DNA
<213> ORGANISM: Homo sapiens

<400> SEQUENCE: 7
caatggatct caccaaagcc aa                      22

<210> SEQ ID NO 8
<211> LENGTH: 30
<212> TYPE: DNA
<213> ORGANISM: Aids-associated retrovirus
<220> FEATURE:
<221> NAME/KEY: misc_feature
<222> LOCATION: (30)..(30)
<223> OTHER INFORMATION: n is dideoxyT

<400> SEQUENCE: 8
agttggagga catcaagcag ccatgcaaan              30

<210> SEQ ID NO 9
<211> LENGTH: 27
<212> TYPE: DNA
<213> ORGANISM: Aids-associated retrovirus
<220> FEATURE:
<221> NAME/KEY: misc_feature
<222> LOCATION: (27)..(27)
<223> OTHER INFORMATION: n is dideoxyT

<400> SEQUENCE: 9
tgctatgtca gttcccttg gttctcn                  27

```
<210> SEQ ID NO 10
<211> LENGTH: 20
<212> TYPE: DNA
<213> ORGANISM: Aids-associated retrovirus

<400> SEQUENCE: 10
atcaatgagg aagctgcaga                                               20
```

DELAYED PYROPHOSPHOROLYSIS ACTIVATED POLYMERIZATION

CROSS-REFERENCE TO RELATED APPLICATIONS

This divisional U.S. patent application claims priority from U.S. non-provisional patent application Ser. No. 16/409,778, filed on May 11, 2019, and further claims priority from U.S. provisional patent application No. 62/683,725, filed on Jun. 12, 2018, each of which is incorporated by reference in its entirety.

SEQUENCE LISTING

This instant application contains a Sequence Listing which has been submitted in ASCII text format via EFS-Web and is hereby incorporated by reference in its entirety. Said ASCII copy is named "SequenceListing_ST25_1.txt" was created on May 21, 2018 and is [2284] bytes in size.

BACKGROUND OF THE INVENTION

Field of the Invention

The present invention relates to the field of molecular biology and particularly pyrophosphorolysis activated polymerization (PAP) for nucleic acid amplification.

Description of the Prior Art

Pyrophosphorolysis Activated Polymerization (PAP)

Pyrophosphorolysis activated polymerization (PAP) is a method for nucleic acid amplification where pyrophosphorolysis and polymerization are serially coupled by DNA polymerase using 3' blocked primers (Liu and Sommer, 2000; Liu and Sommer, 2004b). A primer is blocked at the 3' end with a non-extendable nucleotide (3' blocker), such as a dideoxynucleotide, and cannot be directly extended by DNA polymerase. When the 3' blocked primer anneals to its complementary DNA template, DNA polymerase can remove the 3' blocker from the 3' blocked primer in the presence of pyrophosphate or its analog, and this reaction is called pyrophosphorolysis. The DNA polymerase can then extend the unblocked primer on the DNA template. In addition to references cited herein, PAP has been described in U.S. Pat. Nos. 6,534,269; 7,033,763; 7,105,298; 7,238,480; 7,504,221; 7,914,995 and 7,919,253.

The serial coupling of pyrophosphorolysis and extension using the 3' blocked primer in PAP results in an extremely high selectivity (Liu and Sommer, 2004a; Liu and Sommer, 2004b) because a significant nonspecific amplification (Type II error, resulting in false positive amplification) requires mismatch pyrophosphorolysis followed by mis-incorporation by the DNA polymerase, an event with a frequency estimated to be $3.3 \times 10^{-11}$.

The bi-directional form of PAP (Bi-PAP) is especially suitable for allele-specific amplification that uses two opposing 3' blocked primers with a single nucleotide overlap at their 3' ends (Liu and Sommer, 2004a; Liu and Sommer, 2004b). Bi-PAP can detect one copy of a mutant allele in the presence of $10^9$ copies of the wild type DNA without false positive amplifications.

DNA-PAP

PAP was initially tested with Tfl and Taq polymerases using DNA template of the human dopamine D1 gene, proving the principle that DNA-dependent DNA pyrophosphorolysis and DNA-dependent DNA polymerization can be serially coupled (Liu and Sommer, 2000). The efficiency of PAP was greatly improved using TaqFS, a genetically engineered polymerase comprising a F667Y mutation, which were demonstrated using other DNA templates (Liu and Sommer, 2002).

RNA-PAP (RT-PAP)

RNA-PAP was developed that can directly amplify RNA template without additional treatment. RNA-PAP brings in a new mechanism for amplification of RNA template in which RNA-dependent DNA pyrophosphorolysis removes a 3' blocker such as a dideoxynucleotide from a 3' blocked primer when hybridized to RNA template, and then RNA-dependent DNA polymerization extends the activated primer. Due to this serial coupling, RNA-PAP has high selectivity against mismatches on the RNA template, providing highly specific amplification of RNA template (U.S. Pat. Nos. 9,133,491 and 9,926,543).

PAP with an Acycolonucleotide Blocker and Type II Polymerase

Besides Type I DNA polymerase, we showed that Type II DNA polymerase efficiently catalyzes template-dependent pyrophosphorolysis to activate primers blocked at their 3' termini with acyclonucleotides in which a 2-hydroxyethoxymethyl group substitutes for the 2'-deoxyribofuranosyl sugar. Type II DNA polymerases Vent (exo-) and Pfu (exo-) were used for PAP with 3' acyclonucleotide-blocked primers, besides Type I DNA polymerase (Liu and Sommer, 2004c).

Multiplex-PAP

Advantageous to produce little or no primer-dimer or false priming (Liu and Sommer, 2002), multiple pairs of 3' blocked primers (≥2) were used to amplify multiple potential templates (≥2) located at multiple loci (≥2) in one reaction (Liu, et al., 2006). In an example, multiplex PAP used eight pairs of 3' blocked primers that targeted eight loci in human genome including seven different exons scattered along a 30 Kb sequence of the human factor IX gene and one exon in the human ATM gene.

In addition, multiplex PAP can also use multiple pairs of 3' blocked primers to amplify multiple almost-sequence-identical templates located in one locus in a single reaction, among which the sequence differences may be as little as one base substitution, or a few base deletions or insertions, such as in the KRAS gene (U.S. Pat. Nos. 10,513,727 and 11,193,167).

A Problem of the Large Copy Number of Template in Singleplex Regular-PAP and Our Solution When the copy number of a template is large, e.g., $10^6$ copies, $C_t$ value of a regular-PAP assay is roughly 15, which means the product is accumulated earlier than convenient, causing the amplification to be inaccurate and inconsistent.

Delayed-PAP was developed by introducing an artificial mutation into the 3' region of a 3' blocked primer. Delayed-PAP can delay the product accumulation to a much later time or cycle, overcoming the large copy number problem particularly when taken as an external control.

A Problem of the Minimal-Copy-Ratio of Templates in Multiplex Regular-PAP and Our Solution The minimal-copy-ratio problem often occurs in detecting early stage cancer where minimal copies of somatic cancer-specific mutations are targeted in the presence of large copies of wildtype genome DNA. For example, when the copy number of a target template is small, e.g., 10 copies, but the copy number of an internal control template is large, e.g., 100,000 copies, leading to 1/10,000 minimal-copy-ratio, the multiplex regular-PAP tends to amplify the control consistently but the target inconsistently. This is because product of the internal control accumulates at a much earlier cycle and greatly consumes substrates, e.g., dNTP and polymerase, inhibiting the product accumulation of the target at a much later cycle.

In order to overcome the minimal-copy-ratio problem, delayed-PAP was developed by introducing an artificial mutation into the 3' region of a 3' blocked primer, which can delay the product accumulation to a much later time or cycle. In multiplex format, delayed-PAP is particularly useful to amplify not only the internal control consistently but also the target consistently in the minimal-copy-ratio condition.

SUMMARY OF THE INVENTION

A composition of pyrophosphorolysis activated polymerization (PAP) comprises a first pair of forward and reverse 3' blocked primers and a first template as an external control in a first reaction, in which the first forward or reverse 3' blocked primer has an artificial mutation introduced into the 3' region, so that the product accumulation is substantially delayed in time.

The copy number of the first template is 100,000 or more.

The first product accumulation is substantially delayed, preferably by 10 cycles or more.

Of the first forward or reverse 3' blocked primer, the artificial mutation of the 3' region is a single base substitution that may be A to T, G or C; T to A, G or C; G to A, T or C; or C to A, T or G mutation.

Of the first forward or reverse 3' blocked primer, the artificial mutation of the 3' region ranges from the 3' end to the 10th base from the 3' end, preferably from the 2nd to the 8th base from the 3' end (the 3' end is assigned as the first base from the 3' end).

Of the first forward or reverse 3' blocked primer, the 3' region mismatches the complementary strand of starting template. The mismatch may be G-T, G-G, G-A, C-T, A-A, T-T, A-C or C-C.

The composition of PAP further comprises a second pair of forward and reverse 3' blocked primers and a second template as a target in a second reaction, in which the second forward or reverse 3' blocked primer has no artificial mutations introduced into the 3' region, so that the second product accumulation is not delayed in time.

A composition of multiplex pyrophosphorolysis activated polymerization (PAP) comprises a plurality of pairs of forward and reverse 3' blocked primers and a plurality of templates in a reaction: a) a first pair of forward and reverse 3' blocked primers to amplify a first template as an internal control, in which the first forward or reverse 3' blocked primer has at least an artificial mutation introduced into its 3' region, therefore the first product accumulation is substantially delayed in time, and b) a second pair of forward and reverse 3' blocked primers to amplify a second template as a target in the same reaction, in which the second forward or reverse 3' blocked primer has no artificial mutation introduced into its 3' region, therefore the first product accumulation is not delayed in time.

The copy ratio of the second template as the target to the first template as the internal control is 1/100 or less.

The first product accumulation is delayed, preferably by 10 cycles or more.

Of the first forward or reverse 3' blocked primer, the artificial mutation of the 3' region is a single base substitution that may be A to T, G or C; T to A, G or C; G to A, T or C; or C to A, or T or G mutation.

Of the first forward or reverse 3' blocked primer, the artificial mutation of the 3' region ranges from the 3' end to the 10th base from the 3' end, preferably from the 2nd to the 8th base from the 3' end.

Of the first forward or reverse 3' blocked primer, the 3' region mismatches the complementary strand of starting template. The mismatch may be G-T, G-G, G-A, C-T, A-A, T-T, A-C or C-C.

A method for pyrophosphorolysis activated polymerization (PAP) comprises:
  a) providing a first pair of forward and reverse 3' blocked primers and a first template as an external control in a first reaction, in which the first forward or reverse 3' blocked primer has at least one artificial mutation introduced into its 3' region,
  b) amplifying the first template in the first reaction, and a first product accumulation is delayed in time,
  c) providing a second pair of forward and reverse 3' blocked primers and a second template as a target in a second reaction, in which the second forward or reverse 3' blocked primer has no artificial mutations introduced into its 3' region, and
  d) amplifying the second template in the second reaction, but a second product accumulation is not delayed in time.

Of the method for PAP, the first pair of forward and reverse 3' blocked primers amplifies the first template as the external control in the first reaction, and the copy number of the first template is 10,000 or more.

Of the method for PAP, the first pair of forward and reverse 3' blocked primers amplifies the first template as the external control, and the first product accumulation is delayed by 10 cycles or more.

Of the method for PAP, the first pair of forward and reverse 3' blocked primers amplifies the first template as the external control, and the artificial mutation of the 3' region of the first forward or reverse 3' blocked primer ranges from the 2nd to the 10th base from the 3' end, preferably from the 2nd to the 8th base from the 3' end A method for multiplex pyrophosphorolysis activated polymerization (PAP) comprises:
  a. providing a plurality of pairs of forward and reverse 3' blocked primers and a plurality of potential templates in a reaction, i) of which a first pair of forward and reverse 3' blocked primers amplifies a first template as an internal control, and the first forward or reverse 3' blocked primer has at least one artificial mutation introduced into its 3' region except its 3' end, and ii) of which a second pair of forward and reverse 3' blocked primers amplifies a second template as a target, and the second forward or reverse 3' blocked primer has no artificial mutations introduced into its 3' region, and
  b. amplifying the first and second templates in the same reaction, in which a first product accumulation is delayed in time, but a second product accumulation is not delayed in time.

Of the method for multiplex PAP, the copy ratio of the second template to the first template is 1/100 or less.

Of the method for multiplex PAP, the first product accumulation is delayed by 10 cycles or more.

Of the method for multiplex PAP, the artificial mutation of the 3' region of the first forward or reverse 3' blocked primer ranges from the 2nd to the 10th base from the 3' end, preferably from the 2nd to the 8th base from the 3' end

DETAILED DESCRIPTION OF THE INVENTION

Terminology

Figure 1:
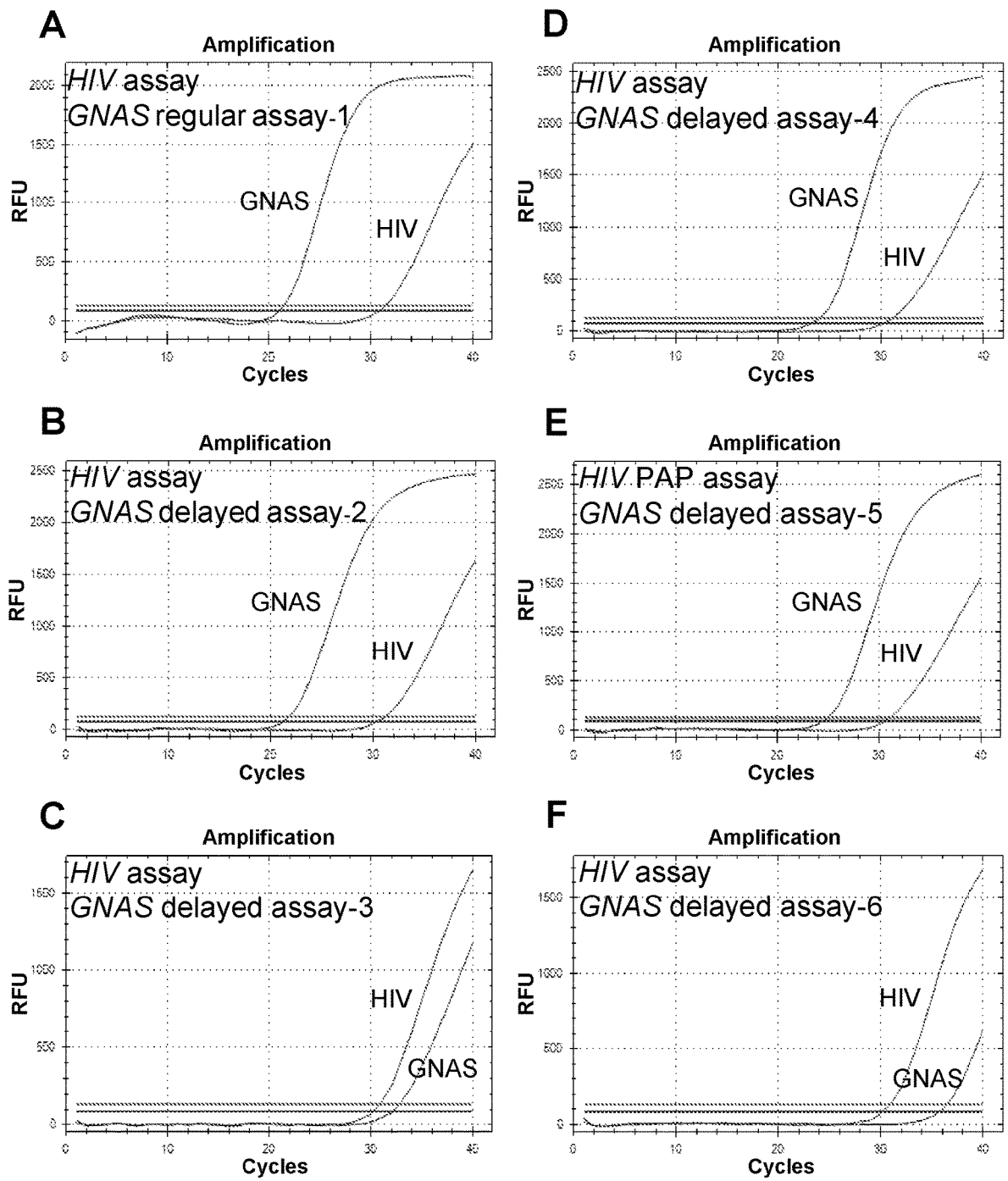
FIG. 1 illustrates multiplex delayed-PAP. A multiplex PAP assay contains a HIV assay as a target and a GNAS assay as an internal control in the same reaction (Panels A to I). Each HIV or GNAS assay includes a forward 3' dideoxynucleotide blocked primer, a reverse 3' dideoxynucleotide blocked primer, and a TaqMan probe with fluorescence reporter FAM or VIC. For the GNAS gene, there are one regular-PAP assay and eight delayed-PAP assays, thus having a total of nine multiplex PAP assays (Table 3). For each reaction, 1,000 copies of HIV plasmid DNA and 330 ng of human wildtype genomic DNA (i.e., 100,000 copies of genome) were amplified for 40 cycles. The amplification plot is shown with the cycle number in X-axis and fluorescence unit in Y-axis for the given cycle. $C_t$ values were obtained for the HIV and GNAS genes in Table 5.
Figure 1:
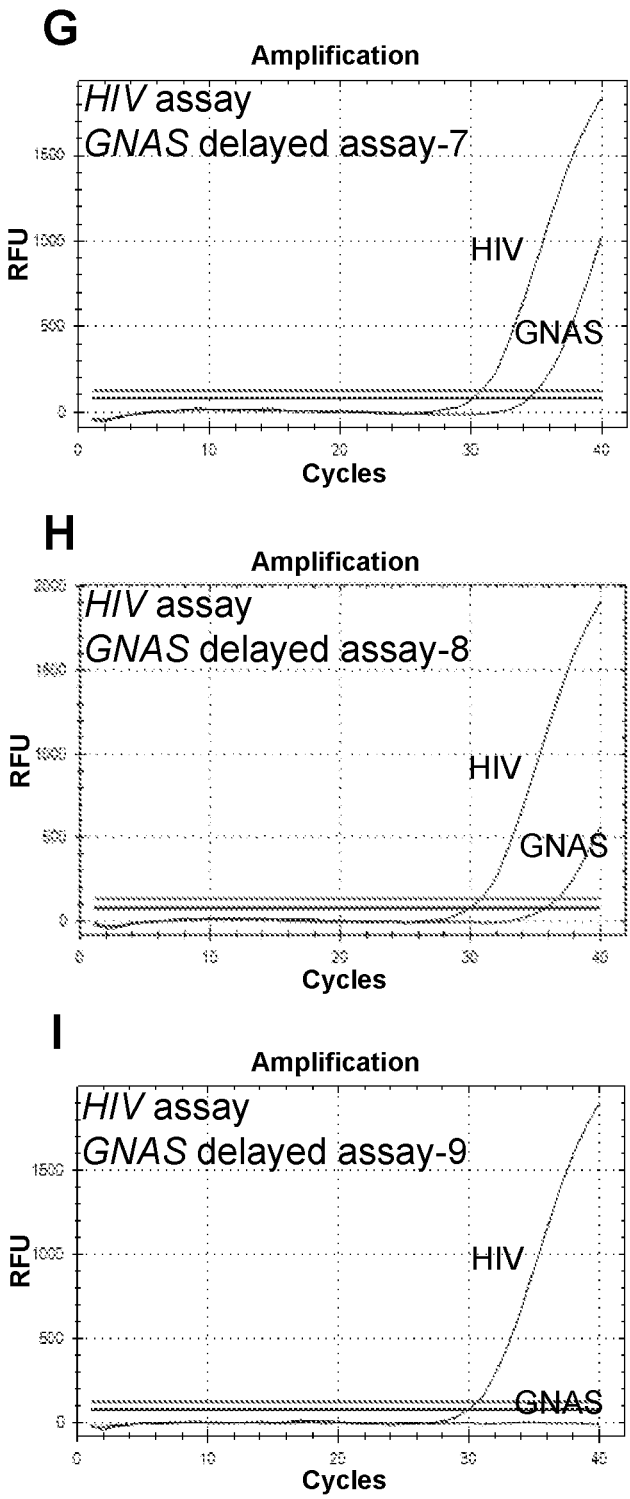

Unless defined otherwise, all technical and scientific terms used herein have the same meaning as commonly understood by one of ordinary skill in the art.

PCR refers to polymerase chain reaction.

Pyrophosphorolysis is the reverse reaction of deoxyribonucleic acid polymerization. In the presence of pyrophosphate, the 3' nucleotide is removed by a polymerase from duplex DNA to generate a triphosphate nucleotide and a 3' unblocked duplex DNA: $[dNMP]_n + PPi \rightarrow [dNMP]_{n-1} + dNTP$ (Deutscher and Kornberg, 1969).

Polymerase or nucleic acid polymerase refers to a polymerase characterized as polymerization or extension of deoxyribonucleic acids.

3' blocked primer refers to an oligonucleotide with a 3' non-extendable nucleotide (3' blocker), such as a dideoxynucleotide or an acycolonucleotide. The 3' nucleotide could not be directly extended, but it can be removed by pyrophosphorolysis and then the unblocked primer can be extended by polymerase.

PAP refers to pyrophosphorolysis activated polymerization.

Delayed pyrophosphorolysis activated polymerization (delayed-PAP) means that the product starts to accumulate at much later time or cycle in the amplification process.

Bidirectional-PAP (Bi-PAP) is a form of PAP that uses a pair of opposing 3' blocked primers that overlap by one nucleotide at their 30 termini.

Exponential-PAP is a form of PAP that uses a pair of two opposing forward and reverse primers for exponential product accumulation with cycles. At least one primer is a 3' blocked primer.

Sensitivity or detection limit is defined as the smallest copy number of a template that generates a detectable product when the 3' blocked primers match the template at the targeted nucleotide, such as the 3' end.

Specificity is defined as the largest copy number of a template that generates an undetectable product when the 3' blocked primers mismatch the template at the targeted nucleotide, such as the 3' end.

Selectivity, the ratio of sensitivity to specificity, is defined as the ability to detect a small number of copies of the matched template in the presence of a large number of copies of the mismatched template without causing false positives.

Thermostable enzyme refers to an enzyme that is heat stable or heat resistant.

TaqFS is a genetic engineered form of Taq polymerase containing G46E and F667Y amino acid changes compared with wild type sequence.

PAP Polymerase is a genetic engineered form of Taq polymerase containing F667Y amino acid changes compared with wild type sequence. It has 5'-3' exonuclease activity, and 5'-3' polymerase activity that can efficiently incorporate ddNTP in extension.

A pair of primers means two opposing forward and reverse primers.

Singleplex PAP means that one pair of primers amplify one template in a reaction.

Multiplex PAP means that ≥2 pairs of primers amplify ≥2 potential templates in a reaction. The multiple templates may be located at multiple loci or at one locus. The sequence differences among the templates, may be as little as one base substitution, a few base deletion or insertion, and may be located as near as at the same nucleotide. In addition, the templates may be completely or partially overlapped within the region.

The 5' region of a primer is the 5' part of the primer sequence, such as the ten successive nucleotides from the 5' end.

The 3' region of a primer is the 3' part of the primer sequence, such as the ten successive nucleotides from the 3' end.

Central region of a primer is the middle part of the primer sequence between the 5' region and the 3' region.

Starting template means the template which is present before amplification starts, such as those of plasmid and genomic DNA.

3'-perfect-match primer means the 3' region has no artificial mutations and perfectly matches the starting template.

Artificial mutation means the mutation that is artificially introduced into primer sequences.

3'-artificial mismatch is formed between the artificial mutation in the 3' region of a 3'-artificial-mutation primer and the complementary strand of a template.

3'-artificial-mutation primer means an artificial mutation is introduced into the 3' region.

Regular-PAP means PAP with two 3'-perfect-match primers.

Multiplex regular-PAP means all PAP assays are regular-PAP assays in the multiplex format.

Delayed-PAP means PAP with one or two 3'-artificial-mutation primers.

Multiplex delayed-PAP means at least one delayed-PAP assay in the multiplex format.

Terminology of Real-Time Fluorescence Detection

Baseline is the level of fluorescence signal during initial cycles. The low level can be considered as background or "noise" of the reaction.

Threshold is defined as the level of fluorescence signal that is a significant higher than baseline signal and can distinguish amplification signal from the background.

$C_t$ (threshold cycle) is the cycle number at which the fluorescence signal crosses the threshold.

Delayed-$C_t$ or $\Delta C_t$ means $C_t$ of delayed-PAP-$C_t$ of regular-PAP when they amplify the same amount of template.

Principle of 3'-Artificial-Mutation Primers for Delayed-PAP

In order to overcome the large copy number and the minimal-copy-ratio problems, a novel design of 3'-artificial-mutation primers was developed each of which contains an artificial mutation in the 3' region. The artificial mutation can be located on one primer or both primers.

1) Twelve Types of Artificial Mutations

Twelve possible types of artificial mutations can be introduced into primers of A to T, G or C; T to A, G or C; G to A, T or C; and C to A, T or G (Table 1). Each artificial mutation causes an artificial mismatch between the primer and the complementary strand of starting template, decreasing efficiency of PAP amplification and thus delaying the product accumulation in time.

Four types of artificial mutations of T to G, C to A, G to T, and C to A were exampled in Table 2.

TABLE 1

Artificial mutations of primers [a]

| No. | Artificial mutation | Resulting mismatch |
|---|---|---|
| 1 | A to T | T-T |
| 2 | A to G | G-T |
| 3 | A to C | C-T |
| 4 | T to A | A-A |
| 5 | T to G | G-A |
| 6 | T to C | C-A |
| 7 | G to A | A-C |
| 8 | G to T | T-C |
| 9 | G to C | C-C |
| 10 | C to A | A-G |
| 11 | C to T | T-G |
| 12 | C to G | G-G |

Footnotes of Table 1.
[a] Twelve possible types of artificial mutations (single-base substitutions) are introduced into primers, resulting in eight types of artificial mismatches between the primers and the complementary strands of starting templates.

2) Eight Types of Artificial Mismatches Between the 3'-Artificial-Mutation Primer and the Complementary Strand of Starting Template The twelve types of artificial mutations always lead to eight types of artificial mismatches between the primers and the complementary strands of starting templates (Table 1).

The mismatches in short DNA duplexes significantly reduce their thermal stabilities, the levels depending on the type of mismatches. The order of thermal stabilities of a total of eight possible mismatches are approximately: G-T>G-G>G-A>C-T>A-A=T-T>A-C=C-C (mismatch G-T=T-G, G-A=A-G, C-T=T-C, and A-C=C-A) (Modrich, 1987) (Aboul-ela, et al., 1985) (Ikuta, et al., 1987).

In the examples, four types of artificial mutations caused three types of artificial mismatches of G-A, T-C, and A-G (Table 2).

3) Locations of Artificial Mutation in the 3' Region of Primers

We localize artificial mutations in the 3' region of primers, ranging from the $1^{st}$ to the $10^{th}$ nucleotide from the 3' end. Besides the types, the locations of mutations also affect thermal stability of mismatches in short DNA duplexes (Modrich, 1987) (Piao, et al., 2008), and thus also affect the efficiency of PAP amplification.

In the examples, four artificial mutations are localized at 3nt and 5nt from the 3' ends of primers (Table 2).

Thus, 3'-artificial-mutation primers for delayed-PAP were developed which can decrease efficiency of PAP amplification because each 3' artificial mutation causes an artificial mismatch between the primer and the complementary strand of starting template (Table 2).

TABLE 2

Primers and probes of the GNAS and HIV-1 genes[a]

| Gene | Primer or probe | | Sequence (5' to 3') (SEQ ID NO) | 3'-artificial mutation[e] | |
|---|---|---|---|---|---|
| | | | | Type | nt from 3' end |
| GNAS gene as control | 3'-perfect-match[b] | Forward-WT | 5'GACTCTGAGCCCTCTTTCCAA ACTACTddC3' (SEQ ID 1) | | |
| | | Reverse-WT | 5'GTCTCAAAGATTCCAGAAGT CAGGACAddC3' (SEQ ID 2) | | |
| | 3'-artificial-mutation[b] | Forward-M1 | 5'GACTCTGAGCCCTCTTTCCAA ACGACTddC3' (SEQ ID 3)[c] | T to G | 5 |
| | | Forward-M2 | 5'GACTCTGAGCCCTCTTTCCAA ACTAATddC3' (SEQ ID 4) | C to A | 3 |
| | | Reverse-M1 | 5'GTCTCAAAGATTCCAGAAGT CAGTACAddC3' (SEQ ID 5) | G to T | 5 |
| | | Reverse-M2 | 5'GTCTCAAAGATTCCAGAAGT CAGGAAAddC3' (SEQ ID 6) | C to A | 3 |
| | | TaqMan probe | 5'VIC-CAATGGATCTCACCAAAGCCA A-MGB3' (SEQ ID 7)[d] | | |
| HIV-1 gene as target | | Forward | 5'AGTTGGAGGACATCAAGCAG CCATGCAAAddT3' (SEQ ID 8) | | |
| | | Reverse | 5'TGCTATGTCAGTTCCCCTTGG TTCTCddT3' (SEQ ID 9) | | |
| | | TaqMan probe | 5'FAM-ATCAATGAGGAAGCT GCAGA-MGB3' (SEQ ID 10)[d] | | |

Footnotes of Table 2.
[a] A PAP assay of the GNAS or HIV gene includes a forward 3' dideoxynucleotide blocked primer, a reverse 3' dideoxynucleotide blocked primer, and a TaqMan probe.
[b] For the GNAS gene, there are two types of primers of 3'-perfect-match and 3'-artificial-mutation.
[c] For this forward-M1 primer, an artificial mutation G is indicated as bold and underlined case. In addition, ddC means dideoxynucleotide C at the 3'end of the primer.
[d] The GNAS TaqMan probe was labeled fluorescence reporter VIC at the 5' end and a quencher MGB at the 3' end. The HIV TaqMan probe was labeled fluorescence reporter FAM at the 5' end and a quencher MGB at the 3' end.
[e] For the 3'-artificial-mutation primers of the GNAS gene, the artificial mutation type and location from the 3' end are also indicated. The nucleotide at the 3' end is assigned as 1.

Example 1 of Materials and Methods

Preparation of Primers

3' ddCMP blocked primers were chemically synthesized in 3'-5' direction and purified by HPLC by Integrated DNA Technologies.

3' ddAMP, ddTMP and ddGMP blocked primers were synthesized enzymatically by adding ddATP, ddTTP and ddGTP to the 3' ends of oligodeoxynucleotides by terminal transferase (Liu and Sommer, 2000; Liu and Sommer, 2002). Then they were purified by 7M urea/16% polyacrylamide gel electrophoresis. The amount of each recovered primer was determined by UV absorbance at 260 nm.

TaqMan probes were synthesized in 3'-5' direction and purified by HPLC by Integrated DNA Technologies. Each probe incorporates a 5' fluorescence reporter of FAM or VIC dye and a 3' nonfluorescence quencher of minor groove binder (MGB).

Preparation of Templates

Genomic DNA was extracted from blood white cells using QIAamp Blood Mini Kit according to Qiagen's protocol.

Recombinant plasmid DNA was constructed by inserting into pUC57 vector a 300 bp HIV target DNA segment which was chemically synthesized. After transformed into E. coli, the recombinant plasmid DNA was extracted using QIAamp Plasmid Mini Kit according to Qiagen's protocol. The eluted DNA was dissolved in TE buffer (10 mM Tris-HCl, 0.1 mM EDTA, pH8.0) and its amount was determined by UV absorbance at 260 nm.

PAP Reaction

Unless stated otherwise, each reaction mixture of 20 µl contained 88 mM Tris-HCl (pH 8.0 at 25° C.), 10 mM $(NH_4)_2SO_4$, 1.2-2.5 mM $MgCl_2$, 25 µM each dNTPs (dATP, dTTP, dGTP and dCTP), 0.1 µM each primers, 0.3 µM TaqMan probe, 90 µM $Na_4PP_i$, 2 units of PAP polymerase, and starting DNA template of wildtype genomic DNA and/or HIV plasmid DNA.

Thermocycling and Fluorescence Detection

A Bio-Rad CFX96 real-time PCR detection system was used for quantification of the amplified product. Analysis mode: fluorophore, Baseline setting: baseline subtracted curve fit, Threshold cycle ($C_t$) determination: single threshold, Baseline method: Auto calculated, Threshold setting: auto calculated. $C_t$ value was thus measured for each reaction which is proportional to the amount of amplified product in the early exponential phase of amplification.

A cycling entailed 96° C. for 12 seconds, 60° C. for 30 seconds, 64° C. for 30 seconds, and 68° C. for 30 seconds for a total of 40 cycles; or another cycling entailed 96° C. for 12 seconds, 64° C. for 45 seconds, and 68° C. for 45 seconds for 40 cycles. A denaturing step of 96° C. for 2 min was added before the first cycle.

Example 2 of Singleplex Delayed-PAP of the GNAS Gene

In singleplex format, there are two types of GNAS assays, depending on primers used. A regular-PAP assay contains a forward and a reverse 3'-perfect-match primers, but a delayed-PAP assay contains at least a 3'-artificial-mutation primer which has an artificial mutation at the 3' region (Tables 2 and 3).

For the GNAS gene, one regular-assay and eight delayed-assays were tested (Table 4). For each reaction, 330 ng of human wildtype genomic DNA (i.e., 100,000 copies of genome) was amplified for 40 cycles.

$C_t$ values of the GNAS assays, the cycle numbers at which fluorescence signals cross threshold, were obtained in Table 4. In order to show how much delayed, delayed-$C_t$ or $\Delta C_t$ values were also calculated in Table 4, each of which is equal to [$C_t$ value of a delayed-PAP assay—$C_t$ value of the regular-PAP assay]. Compared with the regular-PAP assay, $C_t$ values of the delayed-PAP assays were delayed or significantly delayed, ranging from 0.9 to 15.8 cycles, meaning that the product accumulations were delayed by up to more than 30,000 folds.

Thus, a novel design of 3'-artificial-mutation primers was developed in singleplex format, in which delayed-PAP can delay $C_t$ values to much later times or cycles. This singleplex delayed-PAP assay was used as the external control reaction.

Meanwhile, a HIV assay applied two 3'-perfect-match blocked primers without artificial mutations introduced (Table 2) to amplify 1,000 copies of HIV template as a target. Its $C_t$ value was obtained to be around 30 cycles, showing that the HIV product accumulation is not delayed in time.

TABLE 3

One regular-PAP and eight delayed-PAP assays for the GNAS gene [a]

| No. | GNAS gene | Type of PAP | Forward primer | Reverse primer |
|---|---|---|---|---|
| 1 | GNAS assay-1 | Regular-PAP | 3'-pefect-match forward primer WT (SEQ ID No 1) | 3'-pefect-match reverse primer WT (SEQ ID No 2) |
| 2 | GNAS assay-2 | Delayed-PAP | 3'-pefect-match forward primer WT (SEQ ID No 1) | 3'-artificial-mutation reverse primer M1 (SEQ ID No 5) |
| 3 | GNAS assay-3 | Delayed-PAP | 3'-pefect-match forward primer WT (SEQ ID No 1) | 3'-artificial-mutation reverse primer M2 (SEQ ID No 6) |
| 4 | GNAS assay-4 | Delayed-PAP | 3'-artificial-mutation forward primer M1 (SEQ ID No 3) | 3'-pefect-match reverse primer WT (SEQ ID No 2) |
| 5 | GNAS assay-5 | Delayed-PAP | 3'-artificial-mutation forward primer M1 (SEQ ID No 3) | 3'-artificial-mutation reverse primer M1 (SEQ ID No 5) |
| 6 | GNAS assay-6 | Delayed-PAP | 3'-artificial-mutation forward primer M1 (SEQ ID No 3) | 3'-artificial-mutation reverse primer M2 (SEQ ID No 6) |
| 7 | GNAS assay-7 | Delayed-PAP | 3'-artificial-mutation forward primer M2 (SEQ ID No 4) | 3'-pefect-mutation reverse primer WT (SEQ ID No 2) |

TABLE 3-continued

One regular-PAP and eight delayed-PAP assays for the GNAS gene [a]

| No. | GNAS gene | Type of PAP | Forward primer | Reverse primer |
|---|---|---|---|---|
| 8 | GNAS assay-8 | Delayed-PAP | 3'-artificial-mutation forward primer M2 (SEQ ID No 4) | 3'-artificial-mutation reverse primer M1 (SEQ ID No 5) |
| 9 | GNAS assay-9 | Delayed-PAP | 3'-artificial mutation forward primer M2 (SEQ ID No 4) | 3'-artificial-mutation reverse primer M2 (SEQ ID No 6) |

Footnotes of Table 3.
[a] GNAS assay-1 is a regular-PAP and contains two 3'-perfect-match primers. GNAS assays 2 to 4 are Delayed-PAP and each contains one 3'-perfect-match primer and one 3'-artificial-mutation primer. GNAS assays 5 to 9 are Delayed-PAP and each contains two 3'-artificial-mutation primers.

TABLE 4

$C_t$ and $\Delta C_t$ in singleplex delayed-PAP assays of the GNAS gene [a]

| No. | Singleplex | Type of PAP | $C_t$[b] | $\Delta C_t$[b] |
|---|---|---|---|---|
| 1 | GNAS assay-1 | Regular-PAP | 20.2 | 0 |
| 2 | GNAS assay-2 | Delayed-PAP | 21.1 | 0.9 |
| 3 | GNAS assay-3 | Delayed-PAP | 32.1 | 11.6 |
| 4 | GNAS assay-4 | Delayed-PAP | 23.4 | 3.2 |
| 5 | GNAS assay-5 | Delayed-PAP | 24.3 | 4.2 |
| 6 | GNAS assay-6 | Delayed-PAP | 35.4 | 15.8 |
| 7 | GNAS assay-7 | Delayed-PAP | 34.6 | 14.5 |
| 8 | GNAS assay-8 | Delayed-PAP | 35.7 | 15.5 |
| 9 | GNAS assay-9 | Delayed-PAP | NA[b] | NA[b] |

Footnotes of Table 4.
[a] A total of nine GNAS assays were tested as singleplex format including one regular-assay and eight delayed-assays (Table 3). For each reaction, 330 ng of human wildtype genomic DNA (i.e., 100,000 copies of genome) were amplified for 40 cycles.
[b] $C_t$ value of a GNAS assay is indicated as the average of two identical reactions. Delayed-$C_t$ or $\Delta C_t$ value is also indicated.
[c] NA, not available by the end of 40 cycles.

Example 3 of Multiplex Delayed-PAP of the HIV and GNAS Genes

A multiplex PAP assay contains a HIV assay as a target and a GNAS assay as an internal control in the same reaction. For the GNAS gene, one regular-PAP assay and eight delayed-PAP assays were designed. Thus, a total of nine multiplex PAP assays were tested (Tables 2 and 3).

For a multiplex reaction, a regular- or a delayed-assay of the GNAS gene amplified 330 ng of human wildtype genomic DNA (i.e., 100,000 copies of genome) as an internal control, and the HIV assay amplified 1,000 copies of the HIV template as a target in the same reaction (FIG. 1). The copy ratio of the HIV target to GNAS internal control templates is 1/100.

In multiplex format, $C_t$ and $\Delta C_t$ values of the GNAS assays were obtained in Table 5. Compared with the regular-assay, $C_t$ values of the eight delayed-assays were delayed or significantly delayed, ranging from 0.7 to 15.1 cycles later, meaning that the product accumulations were delayed by up to 30,000 folds. In each of the same reactions, $C_t$ values of the HIV assay are also indicated in Table 5, which varied little among the nine multiplex PAP assays.

Furthermore, compared with the nine singleplex GNAS assays in Table 4, the corresponding GNAS assays in multiplex format show similar $C_t$ and $\Delta C_t$ values in Table 5.

Thus, a novel design of 3'-artificial-mutation primers was developed in multiplex format, in which delayed-PAP can delay $C_t$ values to much later times or cycles. This multiplex delayed-PAP was used to amplify not only the internal control consistently but also the target consistently in the minimal-copy-ratio situation.

TABLE 5

$C_t$ and $\Delta C_t$ in multiplex delayed-PAP assays of the HIV and GNAS genes [a]

| No. | Multiplex | $C_t$ of HIV assay[b] | $C_t$ of GNAS assay[b] | $\Delta C_t$ of GNAS assay[c] |
|---|---|---|---|---|
| 1 | HIV assay and GNAS assay-1 | 30.8 | 20.8 | 0 |
| 2 | HIV assay and GNAS assay-2 | 30.4 | 21.5 | 0.7 |
| 3 | HIV assay and GNAS assay-3 | 30.1 | 32.3 | 11.5 |
| 4 | HIV assay and GNAS assay-4 | 30.3 | 23.7 | 2.9 |
| 5 | HIV assay and GNAS assay-5 | 30.3 | 24.5 | 3.7 |
| 6 | HIV assay and GNAS assay-6 | 30.0 | 35.9 | 15.1 |
| 7 | HIV assay and GNAS assay-7 | 30.1 | 34.6 | 13.8 |
| 8 | HIV assay and GNAS assay-8 | 30.0 | 35.9 | 15.1 |
| 9 | HIV assay and GNAS assay-9 | 29.9 | NA[d] | NA[d] |

Footnotes of Table 5
[a] A multiplex PAP assay contains a HIV assay and a GNAS assay. For the GNAS gene, one regular-assay and eight delayed-assays were tested (Table 3). For a reaction, 1,000 copies of HIV plasmid DNA and 330 ng of human wildtype genomic DNA (i.e., 100,000 copies of genome) were amplified for 40 cycles. The copy ratio of the HIV target to GNAS internal control templates is 1/100.
[b] $C_t$ values of the HIV and GNAS assays are indicated as the average of two identical reactions with thresholds of 83 FAM and 99 VIC fluorescence arbitrary units, respectively.
[c] $\Delta C_t$ values of the GNAS assays are also indicated.
[d] NA, not available by the end of 40 cycles.

Example 4 of Application to Multiplex Delayed-PAP Assays of the HIV and GNAS Genes In order to overcome the minimal-copy-ratio problem, a total of nine multiplex PAP assays were tested (Tables 2 and 3). Each multiplex PAP assay contains a HIV assay as a target and a GNAS assay as an internal control in the same reaction. For the GNAS gene, there are one regular-PAP assay and eight delayed-PAP assays.

Four different copy ratios of the HIV target to GNAS internal control templates of 1/10, 1/100, 1/1,000 and 1/10,000 were compared for each multiplex PAP assay. The performance was estimated primarily by consistence of $C_t$ values at a given copy ratio (Table 6).

The multiplex PAP assays 1-8 showed two different categories according to their $\Delta C_t$ values of GNAS assay in Table 5.

1) Category I: The multiplex PAP assays-1, -2, -4, -5 contain the GNAS assays-1, -2, -4, and -5, and their $\Delta C_t$ values of the GNAS gene are 0, 0.7, 2.9, and 3.7, respectively (Table 5). The GNAS assays-1, -2, -4, and -5 performed consistently at the four copy ratios. However, the HIV assay showed the consistency only at the first two copy ratios of 1/10 and 1/100, but not at the last two copy ratios of 1/1,000 and 1/10,000 (Table 6).

2) Category II: The multiplex PAP assays-3, -6, -7, and -8 contain the GNAS assays-3, -6, -7, and -8, and their $\Delta C_t$ values are 11.5, 15.1, 13.8, and 15.1, respectively (Table 5). Both the GNAS assays-3, -6, -7, and -8 and the HIV assay performed consistently at all the four copy ratios from 1/10 to 1/10,000 (Table 6).

Thus, multiplex delayed-PAP, when $\Delta C_t$ values of the GNAS gene >10, can be applied to the minimal-copy-ratio with more consistent performance, presumably because delayed-PAP delays the product accumulation of the GNAS internal control to much later cycles, not yet exhausting substrates, e.g., dNTP and polymerase, for the product accumulation of the HIV target at later cycles.

Thus, a major factor of whether Category I or II is the locations of artificial mutations of 3'-artificial-mutation primers of the GNAS gene which primarily determine how much the product accumulations of the GNAS internal control can be delayed.

TABLE 6

Performance of multiplex delayed-PAP assays of the HIV and GNAS genes [a]

| No. | Multiplex | Copy ratios of HIV target to GNAS internal control templates [b] | | | | Category |
|---|---|---|---|---|---|---|
| | | 1/10 | 1/100 | 1/1,000 | 1/10,000 | |
| 1 | HIV assay and GNAS assay-1 | HIV+, GNAS+[c] | +, + | −, + | −, + | I [d] |
| 2 | HIV assay and GNAS assay-2 | +, + | +, + | −, + | −, + | I |
| 3 | HIV assay and GNAS assay-3 | +, + | +, + | +, + | +, + | II |
| 4 | HIV assay and GNAS assay-4 | +, + | +, + | −, + | −, + | I |
| 5 | HIV assay and GNAS assay-5 | +, + | +, + | −, + | −, + | I |
| 6 | HIV assay and GNAS assay-6 | +, + | +, + | +, + | +, + | II |
| 7 | HIV assay and GNAS assay-7 | +, + | +, + | +, + | +, + | II |
| 8 | HIV assay and GNAS assay-8 | +, + | +, + | +, + | +, + | II |
| 9 | HIV assay and GNAS assay-9 | +, NA | +, NA | +, NA | +, NA | |

Footnotes of Table 6

[a] Performance was primarily estimated by consistence of $C_t$ values at a given copy ratio. + means $C_t$ values are consistent for identical reactions. − means sometimes $C_t$ values vary much and occasionally $C_t$ values are even not present.

[b] Four copy ratios of the HIV target to GNAS internal control templates were tested. 1/10 copy ratio means 10,000 copies of the HIV template to 100,000 copies of the GNAS template in a reaction, 1/100 copy ratio means 1,000 copies of the HIV template to 100,000 copies of the GNAS template, 1/1,000 copy ratio means 100 copies of the HIV template to 100,000 copies of the GNAS template, 1/10,000 copy ratio means 10 copies of the HIV template to 100,000 copies of the GNAS template.

[c] The performance is indicated in the order of the HIV and GNAS assays in the multiplex format.

[d] Multiplex PAP assays 1-8 are divided into I and II categories according to their $\Delta C_t$ values of the GNAS gene in Table 5.

REFERENCE

Aboul-ela F, Koh D, Tinoco I, Jr., Martin F H. 1985. Base-base mismatches. Thermodynamics of double helix formation for dCA3XA3G+dCT3YT3G (X, Y=A,C,G,T). Nucleic Acids Res 13(13):4811-24.

Deutscher M P, Kornberg A. 1969. Enzymatic synthesis of deoxyribonucleic acid. 28. The pyrophosphate exchange and pyrophosphorolysis reactions of deoxyribonucleic acid polymerase. J Biol Chem 244(11):3019-28.

Ikuta S, Takagi K, Wallace R B, Itakura K. 1987. Dissociation kinetics of 19 base paired oligonucleotide-DNA duplexes containing different single mismatched base pairs. Nucleic Acids Res 15(2):797-811.

Liu Q, Nguyen V Q, Li X, Sommer S S. 2006. Multiplex dosage pyrophosphorolysis-activated polymerization: application to the detection of heterozygous deletions. Biotechniques 40(5):661-8.

Liu Q, Sommer S S. 2000. Pyrophosphorolysis-activated polymerization (PAP): application to allele-specific amplification. Biotechniques 29(5):1072-1080.

Liu Q, Sommer S S. 2002. Pyrophosphorolysis-activatable oligonucleotides may facilitate detection of rare alleles, mutation scanning and analysis of chromatin structures. Nucleic Acids Res 30(2):598-604.

Liu Q, Sommer S S. 2004a. Detection of extremely rare alleles by bidirectional pyrophosphorolysis-activated polymerization allele-specific amplification (Bi-PAP-A): measurement of mutation load in mammalian tissues. Biotechniques 36(1):156-66.

Liu Q, Sommer S S. 2004b. PAP: detection of ultra rare mutations depends on P* oligonucleotides: "sleeping beauties" awakened by the kiss of pyrophosphorolysis. Hum Mutat 23(5):426-36.

Liu Q, Sommer S S. 2004c. Pyrophosphorolysis by Type II DNA polymerases: implications for pyrophosphorolysis-activated polymerization. Anal Biochem 324(1):22-8.

Modrich P. 1987. DNA mismatch correction. Annu Rev Biochem 56:435-66.

Piao X, Sun L, Zhang T, Gan Y, Guan Y. 2008. Effects of mismatches and insertions on discrimination accuracy of nucleic acid probes. Acta Biochim Pol 55(4):713-20.

The invention claimed is:

1. A method for multiplex pyrophosphorolysis activated polymerization (PAP), comprising:
   a) providing a plurality of pairs of forward and reverse 3' blocked primers and a plurality of potential templates in a reaction, i) wherein a first pair of forward and reverse 3' blocked primers amplifies a first template as an internal control, and the first forward or reverse 3' blocked primer has at least one artificial mutation introduced into its 3' region except at its 3' end, ii) wherein a second pair of forward and reverse 3' blocked primers amplifies a second template as a target, and the second forward or reverse 3' blocked primer has no artificial mutations introduced into its 3' region, and iii) wherein the copy ratio of the second template to the first template is 1/100 or less, and
   b) amplifying the first and second templates in the same reaction, wherein a first product accumulation is delayed in time, but a second product accumulation is not delayed in time.

2. The method for multiplex PAP of claim 1, wherein the first pair of forward and reverse 3' blocked primers amplifies the first template as the internal control, and wherein the first product accumulation is delayed by 10 cycles or more.

3. The method for multiplex PAP of claim 1, wherein the first pair of forward and reverse 3' blocked primers amplifies the first template as the internal control, and wherein the artificial mutation of the first forward or reverse 3' blocked primer ranges from the 2nd to the 10th base from the 3' end which is assigned as the 1st base.

* * * * *